US012667602B2

(12) United States Patent
Yun et al.

(10) Patent No.: US 12,667,602 B2
(45) Date of Patent: Jun. 30, 2026

(54) COMPOSITION FOR PREVENTING, TREATING OR ALLEVIATING DIABETES, COMPRISING LGI3-DERIVED PEPTIDE AS AN ACTIVE INGREDIENT

(71) Applicant: CHUNG-ANG UNIVERSITY INDUSTRY-ACADEMIC COOPERATION FOUNDATION, Seoul (KR)

(72) Inventors: Hye-Young Yun, Seoul (KR); Dong-Seok Kim, Seoul (KR)

(73) Assignee: CHUNG-ANG UNIVERSITY INDUSTRY-ACADEMIC COOPERATION FOUNDATION, Seoul (KR)

( * ) Notice: Subject to any disclaimer, the term of this patent is extended or adjusted under 35 U.S.C. 154(b) by 1016 days.

(21) Appl. No.: 17/625,437

(22) PCT Filed: Jul. 8, 2020

(86) PCT No.: PCT/KR2020/008879
§ 371 (c)(1),
(2) Date: Jan. 7, 2022

(87) PCT Pub. No.: WO2021/006607
PCT Pub. Date: Jan. 14, 2021

(65) Prior Publication Data
US 2022/0257708 A1 Aug. 18, 2022

(30) Foreign Application Priority Data

Jul. 9, 2019 (KR) ........................ 10-2019-0082713

(51) Int. Cl.
| | |
|---|---|
| *A61K 38/17* | (2006.01) |
| *A61K 38/10* | (2006.01) |
| *A61P 1/16* | (2006.01) |
| *A61P 1/18* | (2006.01) |
| *A61P 3/00* | (2006.01) |
| *A61P 3/10* | (2006.01) |

(52) U.S. Cl.
CPC .......... *A61K 38/1709* (2013.01); *A61K 38/10* (2013.01); *A61P 1/16* (2018.01); *A61P 1/18* (2018.01); *A61P 3/00* (2018.01); *A61P 3/10* (2018.01)

(58) Field of Classification Search
None
See application file for complete search history.

(56) References Cited

U.S. PATENT DOCUMENTS

| | | |
|---|---|---|
| 2009/0221479 A1 | 9/2009 | Barker |
| 2016/0137748 A1 | 5/2016 | Young |
| 2022/0026443 A1* | 1/2022 | Oh ...................... G01N 33/6893 |

FOREIGN PATENT DOCUMENTS

| | | | |
|---|---|---|---|
| KR | 20190135378 A | 12/2019 | |
| WO | 2014202978 A1 | 12/2014 | |
| WO | WO-2020101251 A1 * | 5/2020 | ......... G01N 33/6893 |

OTHER PUBLICATIONS

MedlinePlus, "Metabolic Disorders," available online at https://medlineplus.gov/metabolicdisorders.html, 6 pages (2016) (Year: 2016).*
UniProt Accession No. Q8N145, 13 pages (2002) (Year: 2002).*
Monostra, "Fatty pancreas increases diabetes risk, but may be reversible with weight loss", Healio.com, available online at https://www.healio.com/news/endocrinology/20221202/fatty-pancreas-increases-diabetes-risk-but-may-be-reversible-with-weight-loss, 5 pages (2022) (Year: 2022).*
Radlinger et al., Curr. Diabetes Rep. 20:18 (7 pages) (2020) (Year: 2020).*
Chen et al., Molec. Cellul. Proteomics 7:2323-2336 (2008) (Year: 2008).*
Yin et al., Metabol. Clin. Exp. 57:712-717 (2008) (Year: 2008).*
Tian e al., Biosci. Rep. 38:1-9 (2018) (Year: 2018).*
International Search Report for App. No. PCT/KR2020/008879, dated Oct. 22, 2020, 4 pages.
Kim et al., "Leucine-rich glioma inactivated 3 regulates adipogenesis through ADAM23", Biochimica et Biophysica Acta 1821, 2012, 914-922.
Liu et al., "Nonerythropoietic Erythropoietin-Derived Peptide Suppresses Adipogenesis, Inflammation, Obesity and Insulin Resistance", Scientific Reports, 5:15134, DOI: 10.1038/srep15134, 16 pages, published 2015.

* cited by examiner

*Primary Examiner* — Thea D'Ambrosio
(74) *Attorney, Agent, or Firm* — Riverside Law LLP

(57) ABSTRACT

The present invention relates to a composition and the like, for preventing, treating or alleviating diabetes, comprising an LGI3-derived peptide as an effective component. The composition comprising, as an active ingredient, an LGI3-derived peptide comprising an amino acid sequence represented by SEQ ID NO: 1 or SEQ ID NO: 2 of the present invention exhibits an inhibitory effect on weight gain, elevation of blood glucose levels, pancreas and liver damage, elevation of blood lipid levels, and an increase of insulin resistance indexes accompanied by diabetes and diabetes-associated metabolic disorders associated with diabetes, and thus can prevent, treat, or alleviate diabetes and metabolic disorders associated with diabetes.

2 Claims, 12 Drawing Sheets

Specification includes a Sequence Listing.

FIG. 8

Human/Mouse protein sequence alignment

P25

P34

HIVVDLSA  540  (SEQ ID NO:4)
HVVVDLSA  540  (SEQ ID NO:3)

SEQUENCE LISTING

<160> NUMBER OF SEQ ID NOS: 4

<210> SEQ ID NO 1
<211> LENGTH: 15
<212> TYPE: PRT
<213> ORGANISM: Artificial Sequence
<220> FEATURE:
<223> OTHER INFORMATION: LGI3 derived peptide 25

<400> SEQUENCE: 1

Gln Asn Gly Phe Tyr Ser His Gln Ala Leu His Ala Trp His Arg
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: LGI3 derived peptide 34

<400> SEQUENCE: 2

Asp Glu Gly Arg Gln Lys Phe Val Arg Phe Gln Glu Leu Ala Val
1               5                   10                  15

<210> SEQ ID NO 3
<211> LENGTH: 548
<212> TYPE: PRT
<213> ORGANISM: Artificial Sequence
<220> FEATURE:
<223> OTHER INFORMATION: leucine-rich repeat LGI family member 3
      precursor [Mus musculus] NP_660254.1

<400> SEQUENCE: 3

Met Ala Gly Leu Arg Ala Arg Arg Gly Pro Gly Arg Arg Leu Leu Val
1               5                   10                  15

Leu Ser Thr Leu Gly Phe Cys Leu Met Leu Gln Val Ser Ala Lys Arg
                20                  25                  30

Pro Pro Lys Thr Pro Pro Cys Pro Pro Ser Cys Ser Cys Thr Arg Asp
            35                  40                  45

Thr Ala Phe Cys Val Asp Ser Lys Ser Val Pro Lys Asn Leu Pro Ser
        50                  55                  60

Glu Val Ile Ser Leu Thr Leu Val Asn Ala Ala Phe Ser Glu Ile Gln
65                  70                  75                  80

Asp Gly Ala Phe Ser His Leu Pro Leu Leu Gln Phe Leu Leu Leu Asn
                85                  90                  95

Ser Asn Lys Phe Thr Leu Ile Gly Asp Asn Ala Phe Ile Gly Leu Ser
            100                 105                 110

-continued

```
His Leu Gln Tyr Leu Phe Ile Glu Asn Asn Asp Ile Trp Ala Leu Ser
        115                 120                 125

Lys Phe Thr Phe Arg Gly Leu Lys Ser Leu Thr His Leu Ser Leu Ala
        130                 135                 140

Asn Asn Asn Leu Gln Thr Leu Pro Arg Asp Ile Phe Arg Pro Leu Asp
145                 150                 155                 160

Ile Leu Ser Asp Leu Asp Leu Arg Gly Asn Ala Leu Asn Cys Asp Cys
                165                 170                 175

Lys Val Lys Trp Leu Val Glu Trp Leu Ala His Thr Asn Thr Thr Val
                180                 185                 190

Ala Pro Ile Tyr Cys Ala Ser Pro Pro Arg Phe Gln Glu His Lys Val
                195                 200                 205

Gln Asp Leu Pro Leu Arg Glu Phe Asp Cys Ile Thr Thr Asp Phe Val
        210                 215                 220

Leu Tyr Gln Thr Leu Ser Phe Pro Ala Val Ser Ala Glu Pro Phe Leu
225                 230                 235                 240

Tyr Ser Ser Asp Leu Tyr Leu Ala Leu Ala Gln Pro Gly Ala Ser Ala
                245                 250                 255

Cys Thr Ile Leu Lys Trp Asp Tyr Val Glu Arg Gln Leu Arg Asp Tyr
                260                 265                 270

Asp Arg Ile Pro Ala Pro Ser Ala Val His Cys Lys Pro Met Val Val
                275                 280                 285

Asp Gly Gln Leu Tyr Val Val Val Ala Gln Leu Phe Gly Gly Ser Tyr
        290                 295                 300

Ile Tyr His Trp Asp Pro Asn Thr Thr Arg Phe Thr Lys Leu Gln Asp
305                 310                 315                 320

Ile Asp Pro Gln Arg Val Arg Lys Pro Asn Asp Leu Glu Ala Phe Arg
                325                 330                 335

Ile Asp Gly Asp Trp Phe Phe Ala Val Ala Asp Ser Ser Lys Ala Gly
        340                 345                 350

Ala Thr Ser Leu Tyr Arg Trp His Gln Asn Gly Phe Tyr Ser His Gln
        355                 360                 365

Ala Leu His Ala Trp His Arg Asp Thr Asp Leu Glu Phe Val Asp Gly
        370                 375                 380

Glu Gly Lys Pro Arg Leu Ile Val Ser Ser Ser Ser Gln Ala Pro Val
385                 390                 395                 400

Ile Tyr Gln Trp Ser Arg Ser Gln Lys Gln Phe Val Ala Gln Gly Glu
                405                 410                 415

Val Thr Gln Val Pro Asp Ala Gln Ala Val Lys His Phe Arg Ala Gly
                420                 425                 430

Arg Asp Ser Tyr Leu Cys Leu Ser Arg Tyr Ile Gly Asp Ser Lys Ile
        435                 440                 445

Leu Arg Trp Glu Gly Thr Arg Phe Ser Glu Val Gln Ala Leu Pro Ser
        450                 455                 460

Arg Gly Ser Leu Ala Leu Gln Pro Phe Leu Val Gly Gly His Arg Tyr
465                 470                 475                 480

Leu Ala Leu Gly Ser Asp Phe Ser Phe Thr Gln Ile Tyr Gln Trp Asp
                485                 490                 495

Glu Gly Arg Gln Lys Phe Val Arg Phe Gln Glu Leu Ala Val Gln Ala
                500                 505                 510

Pro Arg Ala Phe Cys Tyr Met Pro Ala Gly Asp Ala Gln Leu Leu Leu
        515                 520                 525

Ala Pro Ser Phe Lys Gly Gln Thr Leu Val Tyr Arg His Val Val Val
```

-continued

```
         530                535                540

Asp Leu Ser Ala
545

<210> SEQ ID NO 4
<211> LENGTH: 548
<212> TYPE: PRT
<213> ORGANISM: Artificial Sequence
<220> FEATURE:
<223> OTHER INFORMATION: leucine-rich repeat LGI family member 3
      precursor [Homo sapiens] NP_644807.1

<400> SEQUENCE: 4

Met Ala Gly Leu Arg Ala Arg Gly Gly Pro Gly Pro Gly Leu Leu Ala
1               5                   10                  15

Leu Ser Ala Leu Gly Phe Cys Leu Met Leu Gln Val Ser Ala Lys Arg
            20                  25                  30

Pro Pro Lys Thr Pro Pro Cys Pro Pro Ser Cys Ser Cys Thr Arg Asp
            35                  40                  45

Thr Ala Phe Cys Val Asp Ser Lys Ala Val Pro Arg Asn Leu Pro Ser
    50                  55                  60

Glu Val Ile Ser Leu Thr Leu Val Asn Ala Ala Phe Ser Glu Ile Gln
65                  70                  75                  80

Asp Gly Ala Phe Ser His Leu Pro Leu Leu Gln Phe Leu Leu Leu Asn
            85                  90                  95

Ser Asn Lys Phe Thr Leu Ile Gly Asp Asn Ala Phe Thr Gly Leu Ser
            100                 105                 110

His Leu Gln Tyr Leu Phe Ile Glu Asn Asn Asp Ile Trp Ala Leu Ser
            115                 120                 125

Lys Phe Thr Phe Arg Gly Leu Lys Ser Leu Thr His Leu Ser Leu Ala
            130                 135                 140

Asn Asn Asn Leu Gln Thr Leu Pro Arg Asp Ile Phe Arg Pro Leu Asp
145                 150                 155                 160

Ile Leu Asn Asp Leu Asp Leu Arg Gly Asn Ser Leu Asn Cys Asp Cys
            165                 170                 175

Lys Val Lys Trp Leu Val Glu Trp Leu Ala His Thr Asn Thr Thr Val
            180                 185                 190

Ala Pro Ile Tyr Cys Ala Ser Pro Pro Arg Phe Gln Glu His Lys Val
            195                 200                 205

Gln Asp Leu Pro Leu Arg Glu Phe Asp Cys Ile Thr Thr Asp Phe Val
            210                 215                 220

Leu Tyr Gln Thr Leu Ala Phe Pro Ala Val Ser Ala Glu Pro Phe Leu
225                 230                 235                 240

Tyr Ser Ser Asp Leu Tyr Leu Ala Leu Ala Gln Pro Gly Val Ser Ala
            245                 250                 255

Cys Thr Ile Leu Lys Trp Asp Tyr Val Glu Arg Gln Leu Arg Asp Tyr
            260                 265                 270

Asp Arg Ile Pro Ala Pro Ser Ala Val His Cys Lys Pro Met Val Val
            275                 280                 285

Asp Ser Gln Leu Tyr Val Val Val Ala Gln Leu Phe Gly Gly Ser Tyr
    290                 295                 300

Ile Tyr His Trp Asp Pro Asn Thr Thr Arg Phe Thr Arg Leu Gln Asp
305                 310                 315                 320

Ile Asp Pro Gln Arg Val Arg Lys Pro Asn Asp Leu Glu Ala Phe Arg
            325                 330                 335
```

-continued

```
Ile Asp Gly Asp Trp Tyr Phe Ala Val Ala Asp Ser Ser Lys Ala Gly
            340             345             350

Ala Thr Ser Leu Tyr Arg Trp His Gln Asn Gly Phe Tyr Ser His Gln
        355             360             365

Ala Leu His Pro Trp His Arg Asp Thr Asp Leu Glu Phe Val Asp Gly
    370             375             380

Glu Gly Lys Pro Arg Leu Ile Val Ser Ser Ser Ser Gln Ala Pro Val
385             390             395             400

Ile Tyr Gln Trp Ser Arg Thr Gln Lys Gln Phe Val Ala Gln Gly Glu
                405             410             415

Val Thr Gln Val Pro Asp Ala Gln Ala Val Lys His Phe Arg Ala Gly
            420             425             430

Arg Asp Ser Tyr Leu Cys Leu Ser Arg Tyr Ile Gly Asp Ser Lys Ile
        435             440             445

Leu Arg Trp Glu Gly Thr Arg Phe Ser Glu Val Gln Ala Leu Pro Ser
    450             455             460

Arg Gly Ser Leu Ala Leu Gln Pro Phe Leu Val Gly Gly Arg Arg Tyr
465             470             475             480

Leu Ala Leu Gly Ser Asp Phe Ser Phe Thr Gln Ile Tyr Gln Trp Asp
            485             490             495

Glu Gly Arg Gln Lys Phe Val Arg Phe Gln Glu Leu Ala Val Gln Ala
            500             505             510

Pro Arg Ala Phe Cys Tyr Met Pro Ala Gly Asp Ala Gln Leu Leu Leu
        515             520             525

Ala Pro Ser Phe Lys Gly Gln Thr Leu Val Tyr Arg His Ile Val Val
    530             535             540

Asp Leu Ser Ala
545
```

COMPOSITION FOR PREVENTING, TREATING OR ALLEVIATING DIABETES, COMPRISING LGI3-DERIVED PEPTIDE AS AN ACTIVE INGREDIENT

CROSS-REFERENCE TO RELATED APPLICATIONS

This application is a U.S. National Phase Application filed under 35 U.S.C. § 371 claiming benefit to International Patent Application No. PCT/KR2020/008879, filed Jul. 8, 2020, which claims the benefit of priority from Korean Patent Application No. 10-2019-0082713, filed Jul. 9, 2019, the contents of each of which are incorporated herein by reference in their entirety.

REFERENCE TO A "SEQUENCE LISTING," A TABLE, OR A COMPUTER PROGRAM LISTING APPENDIX SUBMITTED AS AN ASCII TEXT FILE

The present application hereby incorporates by reference the entire contents of the text file named "206132-0124-00US_Sequence_Listing_ST25.txt" in ASCII format. The text file containing the Sequence Listing of the present application was created on Jan. 6, 2022 and is 10,654 bytes in size.

TECHNICAL FIELD

The present invention relates to a composition for preventing, treating or alleviating diabetes, which includes a leucine-rich repeat LGI family member 3 (LGI3)-derived peptide as an active ingredient.

BACKGROUND ART

Diabetes is caused by a decrease in pancreatic function, such as insulin secretion (type 1 diabetes) or insulin resistance of tissue (type 2 diabetes), and more than 90% cases of diabetes are caused by insulin resistance induced by accumulating an excessive energy source in fat cells and increasing an inflammatory response. According to the World Health Organization (WHO), the prevalence of diabetes in adults worldwide is about 9% and is increasing every year. Diabetes approximately doubles the risk of premature death, and the development of a therapeutic agent for diabetes, which is more effective and has less side effects, compared to the importance of various complications caused by diabetes, is the area with great unmet need. There is active competition around the world to develop a next-generation therapeutic agent for diabetes and enter the global market.

Currently, as a therapeutic agent for diabetes prescribed under FDA approval, insulin administered by injection or a pump is a representative therapeutic agent accounting for about 30% of the total therapeutic agents for diabetes, and other than this, an insulin sensitizer such as metformin or thiazolidinedione, an insulin secretagogue such as sulfonylurea, a peptide derivative such as a glucagon-like peptide-1 (GLP-1) derivative or a dipeptidyl peptidase-4 inhibitor, a renal glucose resorption inhibitor such as a sodium/glucose cotransporter 2 (SGLT2) inhibitor, and α-glucosidase inhibitor are used as a therapeutic agent for diabetes. Insulin has a limited effect on patients with type 1 diabetes who have decreased pancreatic insulin secretion and some patients with type 2 diabetes, and an insulin sensitizer has a limited use in patients with renal failure or acute cardiovascular disease. An insulin secretagogue has a limited use in patients with gestational diabetes or type 1 diabetes, and has a problem of weight gain. A peptide derivative such as GLP-1 has relatively few side effects, but the risk of thyroid cancer and pancreatitis has been raised.

From the above, the unmet needs for therapeutic agents for diabetes having various side effects and limitations require the development of new concept next-generation therapeutic agents for diabetes. Existing oral therapeutic agents for diabetes cause various side effects such as hypoglycemia, weight gain, lactic acidosis, digestive tract disorders, cardiotoxicity and liver toxicity in long-term administration, and do not prevent pancreatic damage and the worsening of insulin resistance. Therefore, there is an urgent need to develop novel drugs which effectively regulate blood sugar without induction of hypoglycemia in long-term administration, and also have effects of pancreas protection, weight loss and improvement in insulin resistance. Recently, like examples of GLP-1 derivatives increased in use, as the clinical effectiveness and potential of peptide-based therapeutic agents for diabetes are high, it is very important to discover novel drug targets and mechanisms, develop peptide-based drugs, and develop a delivery optimization technique in the future.

Gene leucine rich repeat LGI family member 3 or leucine rich glioma inactivated 3 (LGI3) is located on human chromosome 8p21.3, deposited under NCBI Gene ID:203190, has an exon number of 8, and consists of 548 amino acids (NCBI Reference Sequence: NP_644807, SEQ ID NO: 4). In addition, LGI3 cDNA cloned from the brain cDNA library of a mouse (*Mus musculus*) consists of 2931 nucleotides, and consists of 548 amino acids (NCBI Reference Sequence: NP_660254.1, SEQ ID NO: 3) like a human. LGI3 is a protein with a molecular weight of about 60 kDa, having 548 amino acids, and it is difficult to apply LGI3 to the body as it is.

According to studies on LGI3 to date, the diabetes treatment effect of LGI3 by activity control is not known at all.

Based on the above problems, to use the control of LGI3 for diabetic treatment, the inventors discovered an LGI3-derived peptide suitable for application to the human body, and confirmed that the LGI3-derived peptide has an effect of treating and alleviating diabetes in animal models. Thus, the present invention was completed.

DISCLOSURE

Technical Problem

Technical problems to be achieved by the present invention are to provide a novel therapeutic composition that overcomes the side effects and limitations of existing therapeutic agents for diabetes, and at the same time, a composition for treating and alleviating both diabetes and complications caused thereby, and it was confirmed that the composition can be completed by including an LGI3-derived synthetic peptide capable of exhibiting the effect of treating and alleviating diabetes by control of physiological activity of adipokine LGI3.

Therefore, the present invention is directed to providing a pharmaceutical composition for preventing or treating diabetes, comprising an LGI3-derived peptide comprising an amino acid sequence represented by SEQ ID NO: 1 or SEQ ID NO: 2 as an active ingredient.

The present invention is also directed to providing a food composition for preventing or alleviating diabetes, comprising an LGI3-derived peptide comprising an amino acid sequence represented by SEQ ID NO: 1 or SEQ ID NO: 2 as an active ingredient.

The present invention is also directed to providing a pharmaceutical composition for preventing or alleviating one or more diabetes-associated metabolic disorders, comprising an LGI3-derived peptide comprising an amino acid sequence represented by SEQ ID NO: 1 or SEQ ID NO: 2 as an active ingredient.

The present invention is also directed to providing a food composition for preventing or alleviating one or more diabetes-associated metabolic disorders, comprising an LGI3-derived peptide comprising an amino acid sequence represented by SEQ ID NO: 1 or SEQ ID NO: 2 as an active ingredient.

However, technical problems to be solved in the present invention are not limited to the above-described problems, and other problems which are not described herein will be fully understood by those of ordinary skill in the art from the following descriptions.

Technical Solution

To solve the above-described problems, the present invention provides a pharmaceutical composition for preventing or treating diabetes, comprising an LGI3-derived peptide as an active ingredient.

The present invention also provides a food composition for preventing or alleviating diabetes, comprising an LGI3-derived peptide comprising an amino acid sequence represented by SEQ ID NO: 1 or SEQ ID NO: 2 as an active ingredient.

The present invention also provides a method for preventing or treating diabetes, which includes administering an LGI3-derived peptide comprising an amino acid sequence represented by SEQ ID NO: 1 or SEQ ID NO: 2 into a subject.

The present invention also provides a use of an LGI3-derived peptide comprising an amino acid sequence represented by SEQ ID NO: 1 or SEQ ID NO: 2 for preparing a drug for preventing or treating diabetes.

The present invention also provides a use of an LGI3-derived peptide comprising an amino acid sequence represented by SEQ ID NO: 1 or SEQ ID NO: 2 for preventing or treating diabetes.

According to one embodiment of the present invention, the diabetes may be one or more selected from the group consisting of type 1 diabetes, type 2 diabetes, and gestational diabetes.

According to another embodiment of the present invention, the composition may alleviate insulin resistance.

The present invention also provides a pharmaceutical composition for preventing or treating a diabetes-associated metabolic disorder, comprising an LGI3-derived peptide comprising an amino acid sequence represented by SEQ ID NO: 1 or SEQ ID NO: 2 as an active ingredient.

The present invention also provides a food composition for preventing or alleviating a diabetes-associated metabolic disorder, comprising an LGI3-derived peptide comprising an amino acid sequence represented by SEQ ID NO: 1 or SEQ ID NO: 2 as an active ingredient.

The present invention also provides a method for preventing or treating a diabetes-associated metabolic disorder, which includes administering an LGI3-derived peptide comprising an amino acid sequence represented by SEQ ID NO: 1 or SEQ ID NO: 2 into a subject.

The present invention also provides a use of an LGI3-derived peptide, comprising an amino acid sequence represented by SEQ ID NO: 1 or SEQ ID NO: 2, for preparing a drug for preventing or treating a diabetes-associated metabolic disorder.

The present invention also provides a use of an LGI3-derived peptide comprising an amino acid sequence represented by SEQ ID NO: 1 or SEQ ID NO: 2 for preventing or treating a diabetes-associated metabolic disorder.

According to one embodiment of the present invention, the diabetes-derived metabolic disorder may be one or more phenomena selected from the group consisting of hyperglycemia, liver damage, pancreatic damage, and dyslipidemia.

Advantageous Effects

A composition comprising an LGI3-derived peptide as an active ingredient according to the present invention can prevent, treat or alleviate various types of metabolic disorders caused by diabetes by promoting reductions in body weight and blood sugar, which are main causes of diabetes and a diabetes-associated metabolic disorder, reducing pancreatic damage, improving a blood lipid composition and a liver function index, reducing blood insulin and improving insulin resistance.

In addition, the composition of the present invention induces improvements in blood sugar and insulin resistance without an anorectic action, and has an advantage of no or few side effects shown by conventional therapeutic agents for diabetes. Accordingly, the LGI3-derived peptide of the present invention and materials that can be developed by using it as a lead material are expected to be used in various aspects such as compositions for drugs, quasi-drugs, food additives, and fragrances and cosmetics for preventing and treating diabetes and related metabolic disorders thereof.

DESCRIPTION OF DRAWINGS

Figure 8:
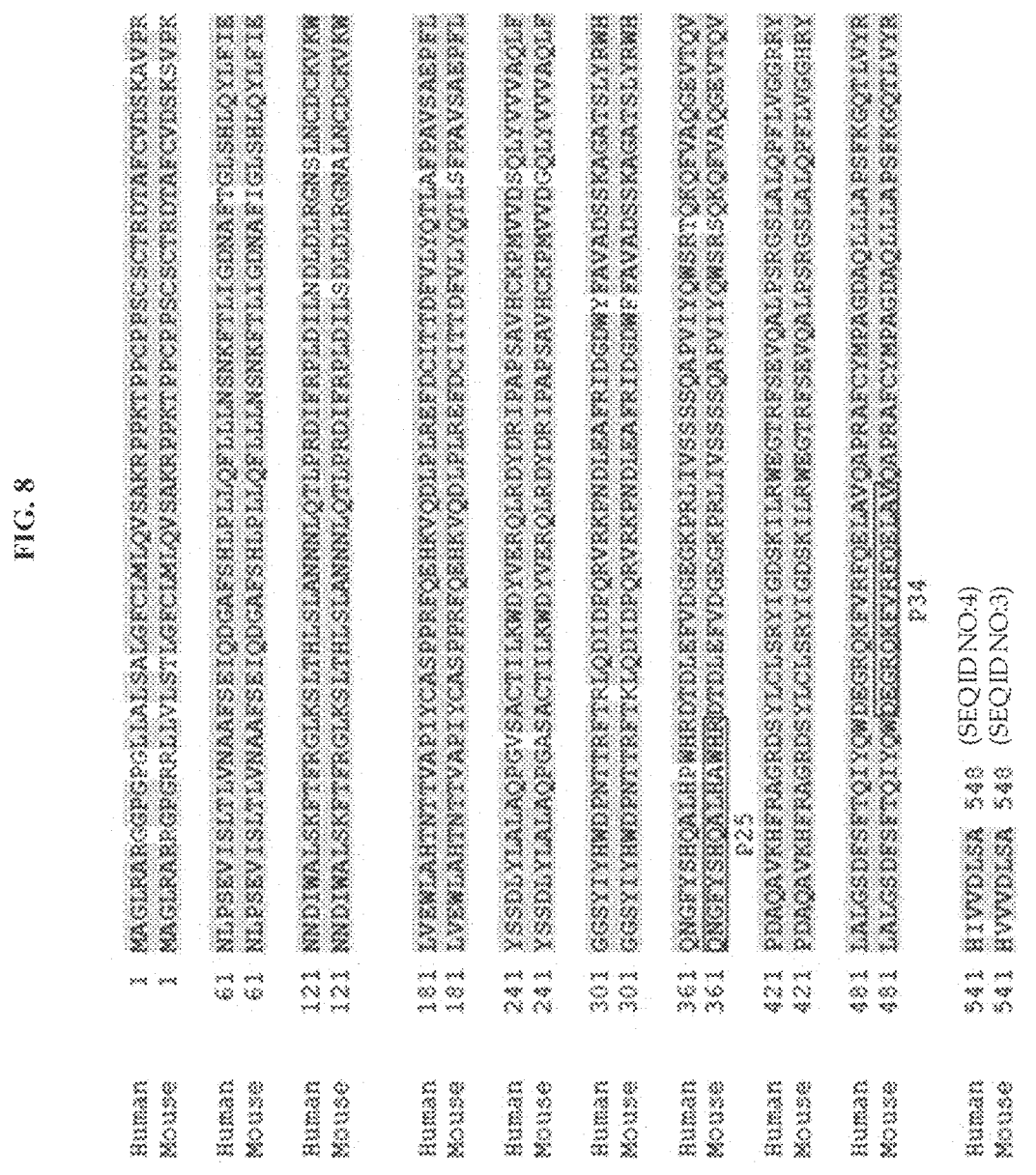

FIG. 8 shows the comparison of amino acid sequences of human and mouse LGI3. The same amino acids in the two species are shown in gray, and the mouse LGI3 sequence corresponding to each of P25 and P34 peptide sequences is shown with a boxed line.

MODES OF THE INVENTION

Figure 1:
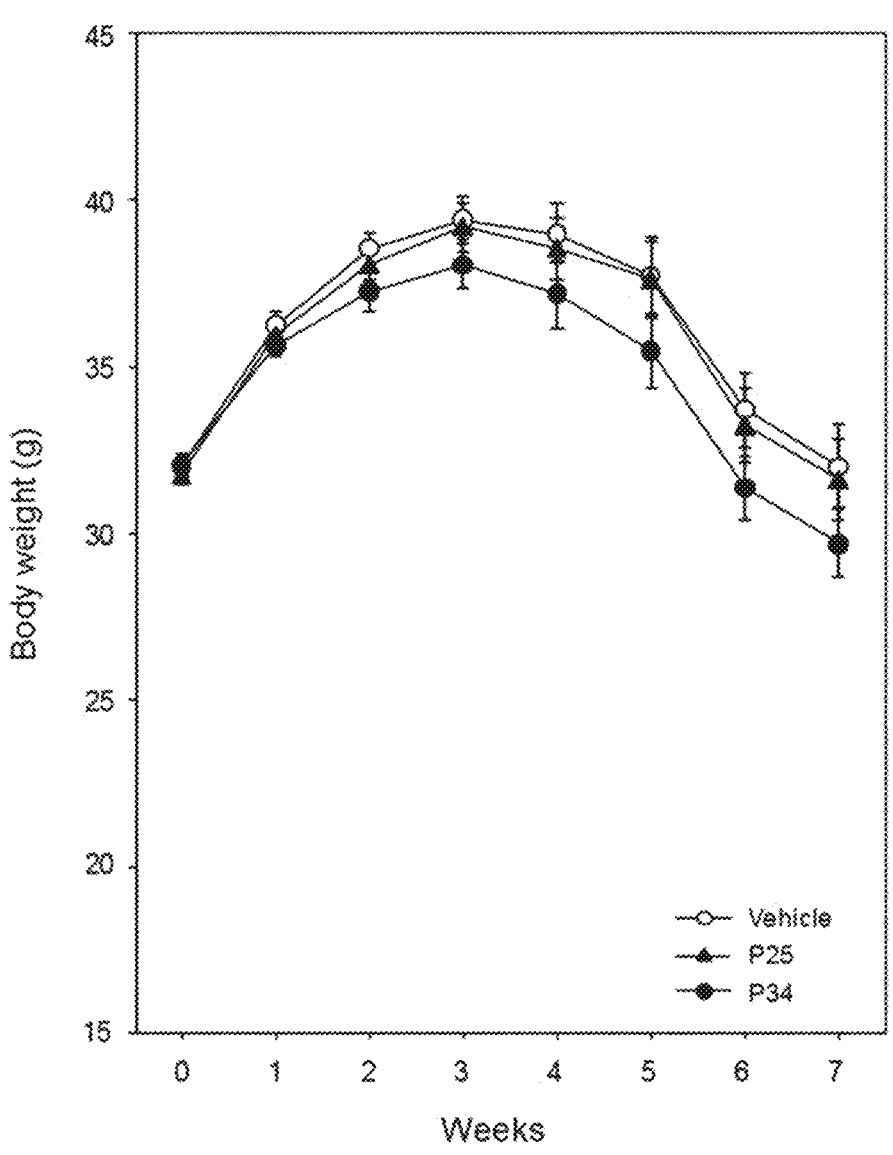
FIG. 1 is a graph confirming a weight loss in P25- and P34-administered db/db mice in comparison with an excipient-administered group.

The inventors studied a new therapeutic target for diabetes to overcome the side effects and limitations of existing therapeutic agents for diabetes. Accordingly, the inventors searched for and found a synthetic LGI3-derived peptide, and confirmed an LGI3-derived peptide comprising an amino acid sequence represented by SEQ ID NO: 1 or SEQ ID NO: 2 has an effect of treating and improving diabetes and a diabetes-associated metabolic disorder through an animal test, and thus the present invention was completed.

Therefore, the present invention provides a pharmaceutical composition for preventing or treating diabetes or a diabetes-associated metabolic disorder, which includes an LGI3-derived peptide comprising an amino acid sequence represented by SEQ ID NO: 1 or SEQ ID NO: 2 as an active ingredient, and a food composition for preventing or alleviating diabetes or a diabetes-associated metabolic disorder, comprising an LGI3-derived peptide comprising an amino acid sequence represented by SEQ ID NO: 1 or SEQ ID NO: 2 as an active ingredient.

In the specification, LGI3, which is an adipokine present only in vertebrates comprising humans, may include an amino acid sequence of SEQ ID NO: 3 or SEQ ID NO: 4. Here, the amino acid sequence of SEQ ID NO: 3 is an amino acid sequence of the LGI3 protein obtained from a mouse, and an amino acid sequence of SEQ ID NO: 4 is an amino acid sequence of the LGI3 protein obtained from a human. The mouse LGI3 amino acid sequence and the human amino acid sequence have 97% homology, and it is obvious that each LGI3-derived peptide can perform the same function in two species.

The "LGI3-derived peptide" used herein is a peptide having an amino acid sequence in a specific region, selected from the LGI3 protein comprising the amino acid sequence of SEQ ID NO: 3 or SEQ ID NO: 4, and the "peptide" used herein is a linear molecule formed by bonding amino acid residues by peptide bonds. The LGI3-derived peptide may be obtained by fragmenting the LGI3 protein, and may be prepared by a chemical synthesis method known in the art, particularly, a solid-phase synthesis technique or liquid synthesis technique.

The LGI3-derived peptide of the present invention may include one or more amino acid alterations in the range showing an effect of preventing, treating and alleviating diabetes.

In the LGI3-derived peptide of the present invention, modification of the N-terminus or the C-terminus may be induced to select a partial region of the amino acid sequence and increase the activity thereof. By such modification, the peptide of the present invention may have an increased half-life upon in-vivo administration.

To the N-terminus of the LGI3-derived peptide of the present invention, a protection group such as an acetyl group, a fluorenyl methoxy carbonyl group, a formyl group, a palmitoyl group, a myristyl group, a stearyl group and polyethylene glycol (PEG) may be bound, and the C-terminus of the peptide may be modified with a hydroxyl —OH) group, an amino (—$NH_2$) group, or an azide (—$NHNH_2$). In addition, fatty acids, oligosaccharide chains, all of nanoparticles (gold particles, liposomes, heparin, hydrogel, etc.), amino acids, or carrier proteins may bind to an end of the peptide of the present invention or an R-group of an amino acid. The above-described amino acid modification may serve to improve the potency and stability of the peptide of the present invention. The term "stability" used herein means not only in vivo stability, but also storage stability (comprising storage stability at room temperature, and in a refrigerator or freezer).

The LGI3-derived peptide of the present invention preferably includes 3 to 30-mer amino acids, and more preferably, 5 to 15-mer amino acids, and as long as the peptide includes a sequence of consecutive amino acids based on any amino acid in the region of $361^{st}$ to $375^{th}$ amino acids, or $496^{th}$ to $510^{th}$ amino acids in the LGI3 protein sequence consisting of the amino acid sequence represented by SEQ ID NO: 3 or SEQ ID NO: 4, the length of the sequence is not limited. When the peptide is too long, there may be difficulty in application of the peptide, and when the peptide is too short, the function thereof my not be performed. The LGI3-derived peptide of the present invention may include an amino acid sequence represented by SEQ ID NO: 1 or SEQ ID NO: 2, or may consist of an amino acid sequence represented by SEQ ID NO: 1 or SEQ ID NO: 2, but the present invention is not limited thereto.

In diabetes, as apoptosis and tissue damage occur by autoimmune destruction of insulin-secreting beta cells in pancreatic islet cells or excessive hypertrophy and oxygen deprivation stress of visceral adipose cells, due to the residues of apoptosis, local inflammation is extended to systemic inflammation, causing insulin resistance in various tissues and leading to impairment of blood sugar control and various complications. In adipose tissue becoming the cause of diabetes in most cases, inflammatory adipokines showing increased secretion are various, such as TNF-α, IL-1, IL-6 and MCP-1, and an anti-inflammatory adipokine showing decreased secretion is adiponectin. Systemic chronic inflammation in diabetic patients induced by these adipokines is also called metabolic inflammation, and not only causes diabetes by reducing tissue sensitivity to insulin, but also disturbs metabolic homeostasis, causing dyslipidemia and various cardiovascular diseases.

Therefore, the inventors attempted to examine the effect of peptides controlling the activity of LGI3 in the LGI3-derived peptide group having an amino acid sequence of SEQ ID NO: 3 on diabetes.

According to an exemplary embodiment of the present invention, the LGI3 protein-derived peptide group having an amino acid sequence of SEQ ID NO: 3 was synthesized, and P25 (SEQ ID NO: 1) and P34 (SEQ ID NO: 2) peptides were selected to confirm the pharmacological effect of the LGI3-derived peptide. To this end, the P25 or P34 was administered to a diabetes animal model such as a db/db mouse, and then a body weight was measured every week. As a result, it was confirmed that, compared to the excipient-administered group, in the P34-administered group, a weight loss effect was about 7%, and in the P25-administered group, there was no significant change in weight (see Example 1-2 and FIG. 1).

Figure 2:
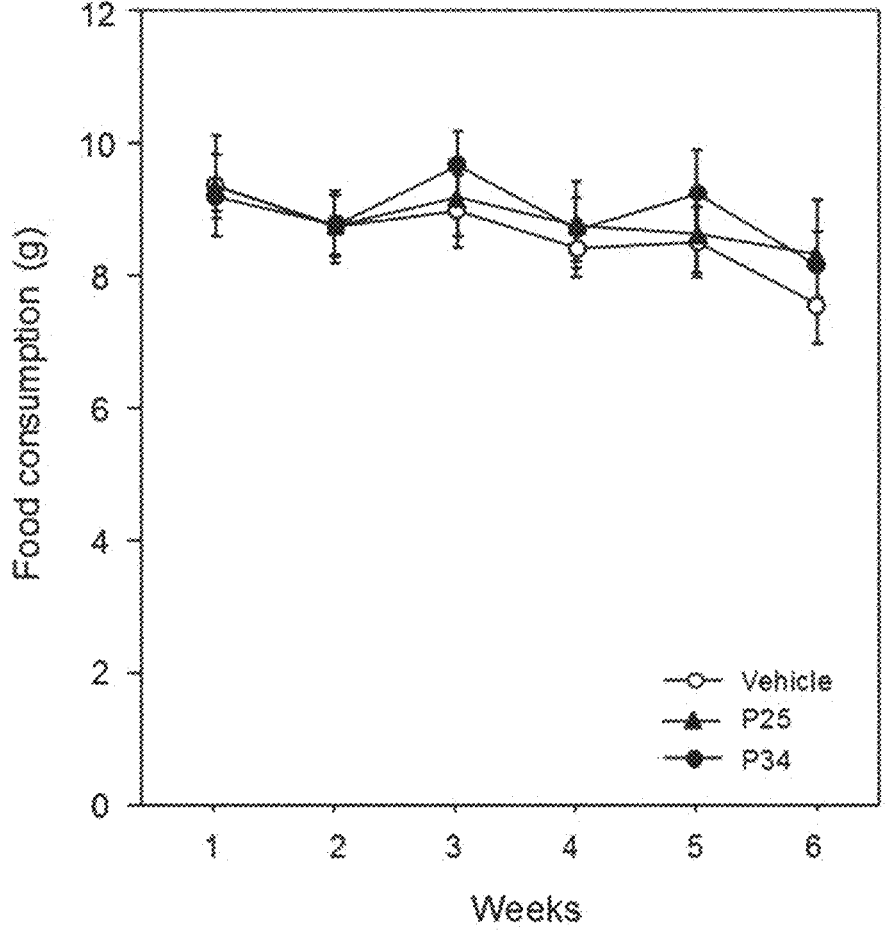
FIG. 2 is a graph confirming that there is no change in feed intake in P25- and P34-administered db/db mice in comparison with an excipient-administered group.

Meanwhile, there was no difference in feed intake in the P25 or P34 peptide-administered group, compared to the excipient-administered group, and it can be seen that the two peptides did not affect the brain appestat (see Example 1-2 and FIG. 2).

In addition, according to an exemplary embodiment of the present invention, the inventors measured blood sugar while the P25 or P34 peptide was administered into the db/db mouse for 6 weeks, confirming blood glucose decreasing effects of about 6 to 9% and about 6 to 11% in the P25-administered group and the P34-administered group, respectively. Both peptides showed a noticeable blood sugar decreasing effect (see Example 1-3 and FIG. 3).

In addition, according to an exemplary embodiment of the present invention, after the P25 or P34 peptide was administered to the db/db mouse for 6 weeks, its effect on the pancreas was investigated. As a result, compared to the excipient-administered group, in both of the P25-administered group and the P34-administered group, it can be confirmed that pancreatic weight increased, and by the P25 or P34 administration, the absolute weight of the pancreas increased about 9%, and the % body weight increased about 10% in the P25-administered group and about 17% in the P34-administered group (see Example 2-1, and FIGS. 4A and 4B).

Figure 5A:
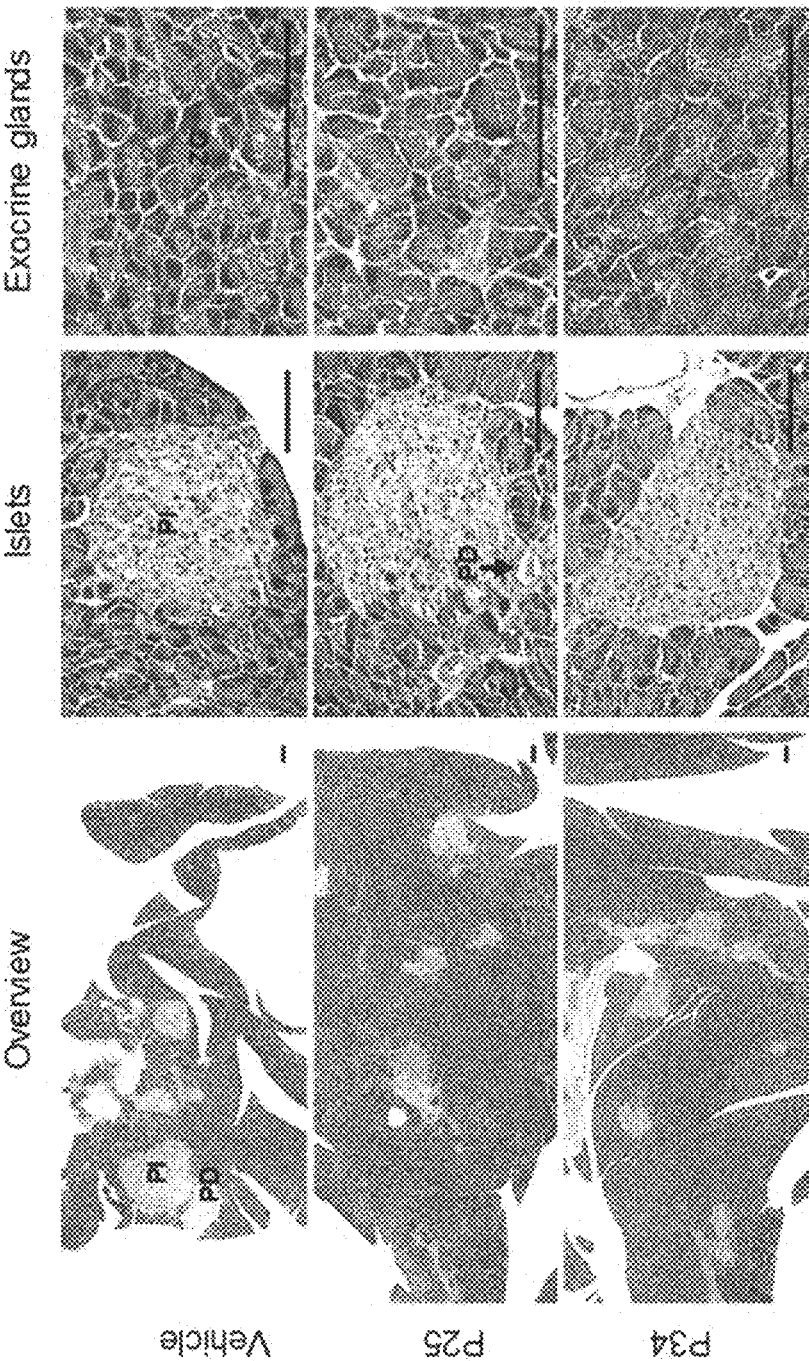
FIG. 5A is a micrograph of a pancreatic tissue section, showing that there is no change in pancreatic islets and the exocrine glands of the pancreas are enlarged in P25- and P34-administered db/db mice in comparison with an excipient-administered group.
Figure 5B:
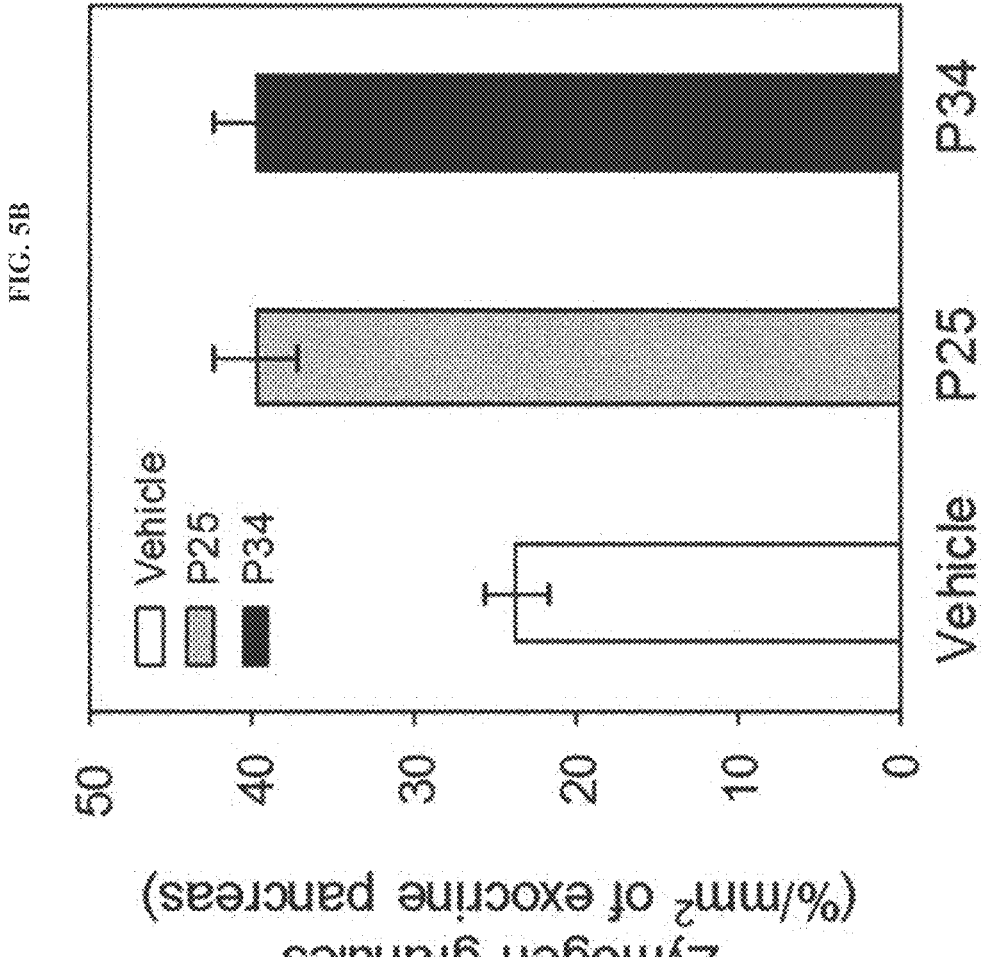
FIG. 5B is a graph confirming a result of increasing zymogen granules of the pancreas in P25- and P34-administered db/db mice in comparison with an excipient-administered group.

In addition, according to one exemplary embodiment of the present invention, hematoxylin-eosin staining (H & E stain) performed for the histopathological examination of the pancreas showed a clear increase in the proportion of zymogen granules per unit area of the pancreatic exocrine (zymogen granules %/mm$^2$ of exocrine) (see Example 2-1, FIGS. 5A and 5B).

In addition, according to an exemplary embodiment of the present invention, after the P25 or P34 peptide was administered to the db/db mouse for 6 weeks, various blood biochemical indices were investigated. Compared to the excipient-administered group, in the P25-administered group and the P34-administered group, it was confirmed that triglyceride (TG), low density lipoprotein (LDL), AST and ALT decreased, and high density lipoprotein (HDL) increased (see Example 2-2 and FIG. 6A). In addition, compared to the excipient-administered group, in the P25-administered group and the P34-administered group, it can be confirmed that a TG/HDL ratio and an LDL/HDL ratio, which are indices of blood lipids, are remarkably reduced and improved (see Example 2-2 and FIG. 6B).

Figure 7A:
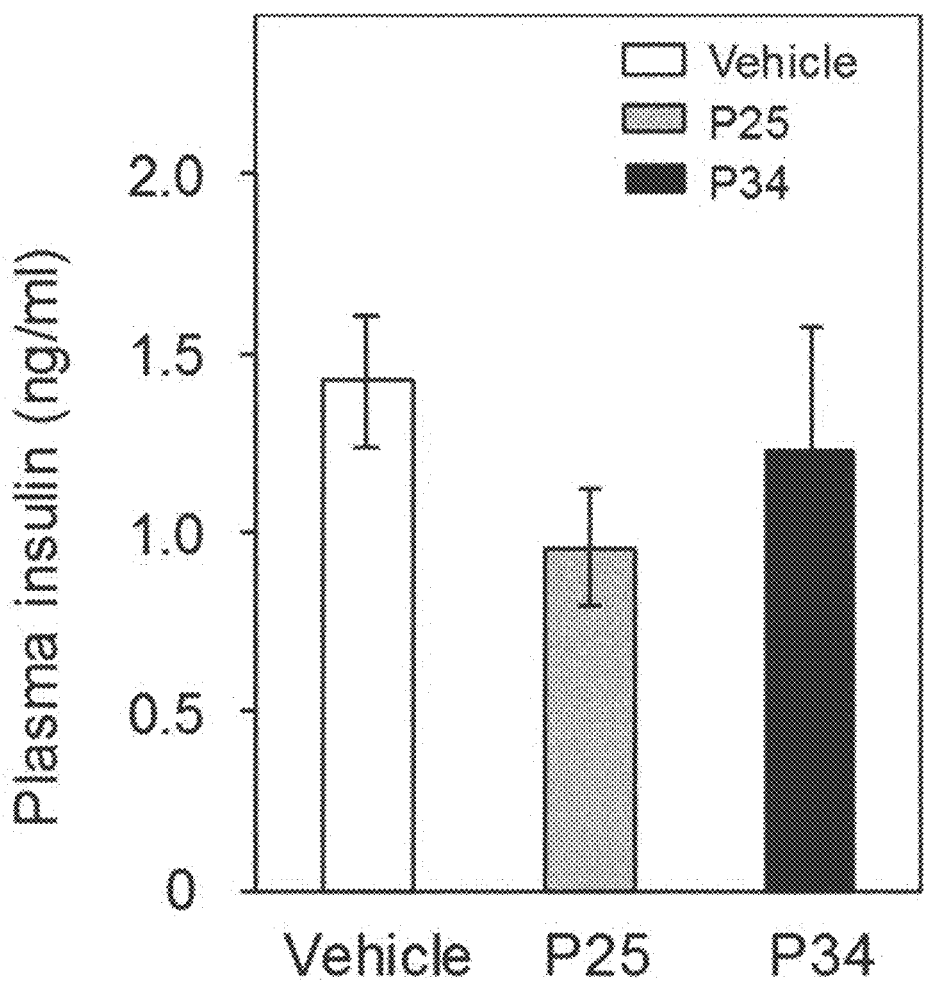
FIG. 7A is a graph confirming that blood insulin is reduced and improved in P25- and P34-administered db/db mice in comparison with an excipient-administered group.
Figure 7B:
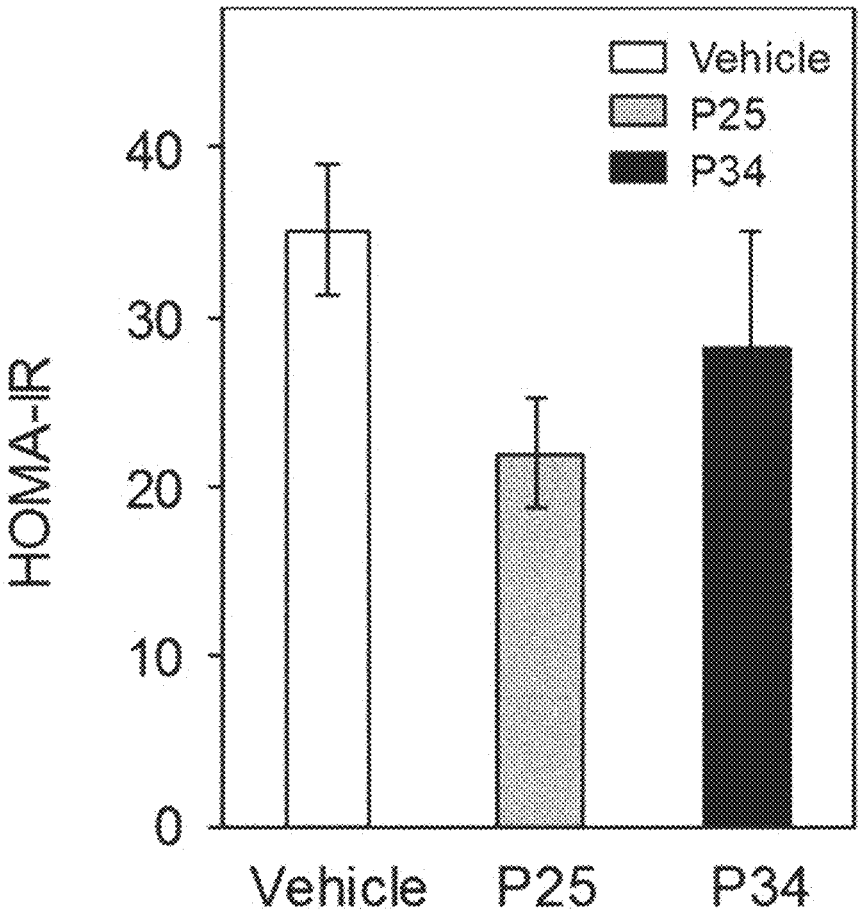
FIG. 7B is a graph confirming that an insulin resistance index (HOMA-IR, Homeostatic model assessment for insulin resistance) is reduced and improved in P25- and P34-administered db/db mice in comparison with an excipient-administered group.

In addition, according to an exemplary embodiment of the present invention, as a result of investigating a blood insulin and insulin resistance index (HOMA-IR) after the P25 or P34 peptide was administered to the db/db mouse for 6 weeks, compared to the excipient-administered group, in the P25-administered group and the P34-administered group, it was confirmed that the HOMA-IR is reduced and improved (see Example 2-3, FIGS. 7A and 7B).

From the above result, the inventors confirmed that the LGI3-derived peptides P25 and P34 reduce blood sugar and improve the insulin resistance index, exhibiting an effect of preventing or treating diabetes, and an effect of improving a diabetes-associated metabolic disorder such as pancreatic damage, dyslipidemia, and liver damage.

In addition, both of the P25 and P34 peptides have suitable sizes for application to the human body, exhibit high solubility in water (P25, 10 mg/ml; P34, 1 mg/ml), and thus facilitate formulation and administration.

Unlike existing therapeutic agents for diabetes, the composition comprising an LGI3-derived peptide according to the present invention exhibits an effect of improving indicators of diabetes and diabetes-associated metabolic disorders by controlling the activity of LGI3, which is an adipokine secreted from adipose tissue. Therefore, it can be used as a novel (first-in-class) therapeutic agent for diabetes based on LGI3, which overcomes the side effects and limitations shown from existing drugs or a lead material for development of a therapeutic agent, and can be used for health functional foods for modern people whose diets causing metabolic diseases are prevalent.

In addition, since the effect of losing weight and improving indicators of diabetes by administration of an LGI3-derived peptide was confirmed, it is assumed that metabolic disorders related to diabetes can be alleviated due to the increases in adipose cell differentiation and insulin sensitivity by controlling LGI3's functions of inhibiting the differentiation of adipose cells and controlling metabolic inflammation, and the functional improvement in subcutaneous fat and the reduction in visceral and liver fats through absorption of blood glucose and increased fat storage capacity. That is, in diabetic patients, the composition comprising an LGI3-derived peptide according to the present invention generally treats diabetes through recovery from accumulation of excessive adipose tissue, deficient differentiation capacity of adipose cells and increased metabolic inflammation, and is differentiated from existing anti-diabetic substances.

Collectively, the LGI3-derived peptide of the present invention can be used in a pharmaceutical composition for preventing or treating diabetes, and used as a lead material for the development of a therapeutic agent for diabetes. In addition, the LGI3-derived peptide of the present invention may be used in a food composition for preventing or alleviating diabetes, and pancreatic and liver damage and dyslipidemia, induced by diabetes.

The LGI3-derived peptide of the present invention may be included at 1 pg to 30 g w/v % in a composition for preventing, treating or alleviating diabetes and a diabetes-associated metabolic disorder, but the present invention is not limited thereto.

In addition, the present invention may provide a method of preventing, treating or alleviating diabetes or a diabetes-associated metabolic disorder, which includes administering a composition comprising an LGI3-derived peptide comprising an amino acid sequence represented by SEQ ID NO: 1 or SEQ ID NO: 2 as an active ingredient into a subject.

The term "administration" used herein refers to introduction of a pharmaceutical composition of the present invention by any appropriate method to a patient, and the administration route of the composition of the present invention may be various, for example, oral or parenteral, as long as the composition of the present invention can reach target tissue.

The term "subject" used herein refers to a target into which the LGI3-derived peptide of the present invention, or a pharmaceutical composition comprising the same can be administered, and there is no limit to a target. The subject used herein is preferably a mammal including a human, for example, a mammal such as a human, a mouse, a rat, a monkey, a cat, a dog, a cow or a pig, but the present invention is not limited thereto.

The "prevention" used herein refers to all actions of delaying the hypertrophy of adipose tissue or a metabolic disorder thereby by the administration of the composition of the present invention, the "treatment" used herein refers to all actions involved in alleviating or beneficially changing symptoms of diabetes or a metabolic disorder thereby by the administration of the pharmaceutical composition according to the present invention, and the "alleviation" means all actions that reduce parameters associated with diabetes or a metabolic disorder induced by a high fat diet, for example, the degree of symptoms, by the administration of the composition according to the present invention.

The "diabetes" used herein is a metabolic disorder syndrome characterized by the lack of insulin hormone produced from the beta cells of the pancreas or insulin resistance, and further hyperglycemia resulting from the deficiency of both. The diabetes may be classified into insulin-dependent diabetes (IDDM, type 1) and non-insulin-dependent diabetes (NIDDM, type 2) caused by impairment of insulin resistance and insulin secretion. In both type 1 and type 2 diabetes, various complications such as a heart disease, an intestinal disease, an eye disease, a kidney disease, a neurological disease, and stroke occur, leading to chronic neurological diseases and cardiovascular diseases due to long-term increased blood sugar and insulin levels, and acute complications due to short-term hypoglycemia and hyperglycemia. Diabetes causes chronic hyperglycemia, and also causes disorders of lipid and protein metabolism as well as carbohydrate metabolism. The conditions are diverse, and are directly caused by hyperglycemia, and include diabetic peripheral neuropathy, diabetic retinopathy, diabetic nephropathy, diabetic cataract and keratosis, diabetic arteriosclerosis in the retina, kidneys, nerves and cardiovascular system.

The "diabetes-associated metabolic disorder" used herein refers to symptoms resulting from hyperglycemia resulting from, caused, derived, or associated with diabetes and disorders of lipid or protein metabolism, and usually, is the generic term for hyperglycemia, pancreatic and liver damage, caused by disorders of glucose and lipid metabolism. More specifically, the "pancreatic and liver disease" refers to a failure of the pancreas or liver to function due to extrinsic or intrinsic factors, and the "blood lipid abnormality" used herein means that an increase in total blood cholesterol, low density lipoprotein-cholesterol, or a triglyceride, or a decrease in high density lipoprotein-cholesterol, compared to a normal condition. That is, the diabetes-associated metabolic disorders may be, but are not limited to, one or more phenomena selected from the group consisting of hyperglycemia, liver damage, pancreatic damage and dyslipidemia, and the pancreatic damage may include pancreatic exocrine hypothyroidism.

The pharmaceutical composition according to the present invention may further include a suitable carrier, excipient and diluent, which are conventionally used in preparation of a pharmaceutical composition.

The "carrier" used herein is also called a vehicle, referring to a compound facilitating the addition of a protein or peptide into cells or tissue. For example, dimethyl sulfoxide (DMSO) is a carrier generally used to make more organic materials enter cells or tissue of an organism.

The "diluent" used herein is defined as a compound which not only stabilizes the biologically active form of a target protein or peptide, but also dilutes the protein or peptide in water. Salts dissolved in a buffer solution are used as diluents in the art. A conventionally used buffer solution is phosphate buffered saline, which is because it mimics a salt state of human body fluid. Since the buffered salt can control the pH of a solution at a low concentration, it is rare for a buffer diluent to change the biological activity of a compound. Compounds containing azelaic acid, used herein, are pharmaceutical compositions, which may be administered alone, or administered after being mixed with other ingredients or suitable carriers or excipients as in combination therapy.

In addition, the pharmaceutical composition for preventing or treating diabetes, comprising the LGI3-derived peptide as an active ingredient, according to the present invention may be used in the form of a powder, a granule, a tablet, a capsule, a suspension, an emulsion, a syrup, a preparation for external use such as an aerosol, or a sterilized injectable solution according to a conventional method, and the carrier, excipient and diluent which may be included in the pharmaceutical composition according to the present invention may include lactose, dextrose, sucrose, an oligosaccharide, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methyl hydroxybenzoate, propyl hydroxybenzoate, talc, magnesium stearate and mineral oil. In formulation, generally used diluents or excipients such as fillers, extenders, binders, wetting agents, disintegrants and surfactants are used. A solid formulation for oral administration may be a tablet, pill, powder, granule or capsule, and such a solid formulation may be prepared by mixing at least one of excipients, for example, starch, calcium carbonate, sucrose, lactose and gelatin, with the active ingredient. Also, in addition to the simple excipient, lubricants such as magnesium stearate and talc may also be used. As a liquid formulation for oral administration, a suspension, a liquid for internal use, an emulsion, or a syrup may be used, and a generally-used simple diluent such as water or liquid paraffin, as well as various types of excipients, for example, a wetting agent, a sweetener, a fragrance and a preservative may be included. A formulation for parenteral administration may be a sterilized aqueous solution, a non-aqueous solvent, a suspension, an emulsion, a lyophilized preparation or a suppository. As the non-aqueous solvent or suspension, propylene glycol, polyethylene glycol, a vegetable oil such as olive oil, or an injectable ester such as ethyl oleate may be used. As a suppository base, Witepsol, Tween 61, cacao butter, laurinum, or glycerogelatin may be used.

The pharmaceutical composition of the present invention may be administered orally or parenterally, preferably, parenterally, and in the case of parenteral administration, muscular injection, intravenous injection, subcutaneous injection, intraperitoneal injection, local administration or transdermal administration may be used.

A suitable dose of the pharmaceutical composition of the present invention may vary depending on factors such as a formulation method, an administration method, a patient's age, weight or gender, a pathological condition, a diet, administration time, an administration route, an excretion rate and reaction sensitivity.

The pharmaceutical composition of the present invention may be prepared in the form of a unit dose or in a large-capacity container by formulation with a pharmaceutically acceptable carrier and/or excipient according to a method easily performed by those of ordinary skill in the art to which the invention belongs. Here, the pharmaceutical composition of the present invention may be formed in the form of a solution, suspension or emulsion in an oil or aqueous medium, an extract, a powder, a granule, a tablet or a capsule, and may further include a suspending agent or a stabilizer.

Moreover, the present invention provides a food composition comprising an LGI3-derived peptide comprising an amino acid sequence represented by SEQ ID NO: or SEQ ID NO: 2 as an active ingredient. In addition, the LGI3-derived peptide comprising an amino acid sequence represented by SEQ ID NO: 1 or SEQ ID NO: 2 may be added to foods for alleviating symptoms of diabetes or a diabetes-associated metabolic disorder. In the present invention, foods include all functional foods including functional foods and health functional foods. When the LGI3-derived peptide of the present invention is used as a food additive, the LGI3-derived peptide may be used alone or in combination with another food or food ingredient, and may be suitably used by a conventional method. The mixing amount of the active ingredient may be appropriately determined according to the purpose of use (prevention, health or therapeutic treatment). Generally, in production of foods or beverages, the LGI3-derived peptide of the present invention may be added at 15 wt % or less, and preferably 10 wt % or less with respect to the raw materials. However, in long-term consumption for health and hygiene or health control, the amount of the composition may be the same as or lower than the above-mentioned range.

There is no particular limit to the type of food. Examples of the foods to which the above-described materials can be added include meat, sausage, bread, chocolate, candy, snack, confectionery, pizza, ramen, other noodles, gum, dairy products including ice cream, various soups, beverages, tea, drinks, alcoholic beverages and a vitamin complex, and in an ordinary sense, all health functional foods are included.

The health beverage composition according to the present invention may contain various flavoring agents or natural carbohydrates as additional ingredients, like a common beverage. include conventional sugars, for example, monosaccharides such as glucose, fructose, etc.; disaccharides such as maltose, sucrose, etc.; and polysaccharides such as dextrin, cyclodextrin, etc., and sugar alcohols such as xylitol, sorbitol, erythritol, etc. As a sweetener, natural sweeteners such as thaumatin and a stevia extract, or a synthetic sweetener such as saccharin or aspartame may be used. The proportion of the natural carbohydrate is generally about 0.01 to 0.20 g, and preferably, about 0.04 to 0.10 g per 100 mL of the composition of the present invention.

In addition, the composition of the present invention may contain various nutrients, vitamins, electrolytes, flavoring agents, pectic acid and a salt thereof, alginic acid and a salt thereof, organic acids, protective colloidal thickening agents, pH adjustors, stabilizers, preservatives, glycerin, alcohols, or carbonizing agents used in carbonated beverages. Other than these, the composition of the present invention may contain fruit pulp for producing natural fruit juices, fruit drinks and vegetable drinks. The proportions of these additives are not critical, but are generally selected in the range of 0.01 to −0.20 parts by weight with respect to 100 parts by weight of the composition of the present invention.

In addition, the present invention provides a use of an LGI3-derived peptide, comprising an amino acid sequence represented by SEQ ID NO: 1 or SEQ ID NO: 2 for preparing a drug for preventing or treating diabetes.

In addition, the present invention provides a use of the LGI3-derived peptide, comprising an amino acid sequence represented by SEQ ID NO: 1 or SEQ ID NO: 2 for preparing a drug for preventing or treating a diabetes-associated metabolic disorder.

As the present invention may have various modifications and embodiments, specific embodiments the present invention will be described in further detail below. However, the present invention is not limited to the specific embodiments, and it should be understood that the present invention includes all modifications, equivalents and alternatives included in the technical idea and scope of the present invention. To explain the present invention, if it is determined that a detailed description of the related art may obscure the gist of the present invention, the detailed description thereof will be omitted.

Hereinafter, to help in understanding the present invention, exemplary examples will be suggested. However, the following examples are merely provided to more easily understand the present invention, and not to limit the present invention.

EXAMPLES

Example 1. Confirmation of Effect of LGI3-Derived Peptide on Weight, Feed Intake and Blood Sugar in Diabetic Animal Model

Example 1-1. Preparation of Diabetic Animal Models and Administration of Test Materials As laboratory animals, specific pathogen-free (SPF) db/db mice (C57BLKS/J-db/dbC57BL/6i, male, Central Lab. Animal Inc., Korea) were used. The animals were fed under a temperature of 23±3° C., a relative humidity of 55±15%, with a ventilation frequency of 10 to 20 times/hr, 12-hour lighting and an illuminance of 150 to 300 Lux. As feed, solid feed for rodents (Teklad certified irradiated global 18% protein rodent diet; 2918C, ENVIGO, UK) was provided ad libitum.

The laboratory animals were weighed for ranking and randomly allocated to the following groups such that an average weight of each group was distributed as evenly as possible according to the ranked weights: an excipient (vehicle)-administered group (phosphate buffered saline as an excipient, Welgene, Korea) as a control, a P25 (SEQ ID NO: 1)-administered group, and a P34 (SEQ ID NO: 2)-administered group. There were 8 animals per group. The LGI3-derived peptide was administered intraperitoneally once/day, twice/week, and a total of 12 times for 6 weeks. A dose of the LGI3-derived peptide was 10 mg/kg, and a dosage thereof was 10 ml/kg/day.

After the administration of the LGI3-derived peptide, types of general symptoms and the severity of symptoms were observed once a day, and as a result of observation of general symptoms during the test period, no abnormal symptoms or dead animals were observed in all groups. The animals were weighed at the time of acquisition, group division, the initiation of administration and autopsy, and at other times, weighed once a week. An amount of feed intake was measured once a week during the administration period. For blood glucose measurement, the animals were fasted (water provided) for about 6 hours before the measurement. Blood glucose was measured using a blood glucose meter (G-Doctor, Green Cross) on the measurement day, and measured once a week.

Example 1-2. Confirmation of Effect of Administration of LGI3-Derived Peptide on Weight and Appetite To confirm the effect of the P25 or P34 administered into the db/db mice in Example 1-1 on weight and appetite, a weekly weight and feed intake were checked.

As a result, as shown in FIG. 1, a weight loss effect was confirmed in the P34-administered group. More specifically, an approximate 6 to 7% weight loss was confirmed at week 5 to 7 in the P34-administered group.

On the other hand, as confirmed in FIG. 2, there was no feed intake difference in the P25- and P34-administered groups, compared to the excipient-administered group. This result indicates that in the P25- or P34-administered group, there is no effect on the appetite of the individual, and a weight increase is inhibited in the P34-administered group.

Example 1-3. Confirmation of Effect on Blood Glucose by Administration of LGI3-Derived Peptide To confirm the effect of the P25 or P34 administered into the db/db mice in Example 1-1 on blood sugar, blood sugar was measured by the method described in Example 1-1.

Figure 3:
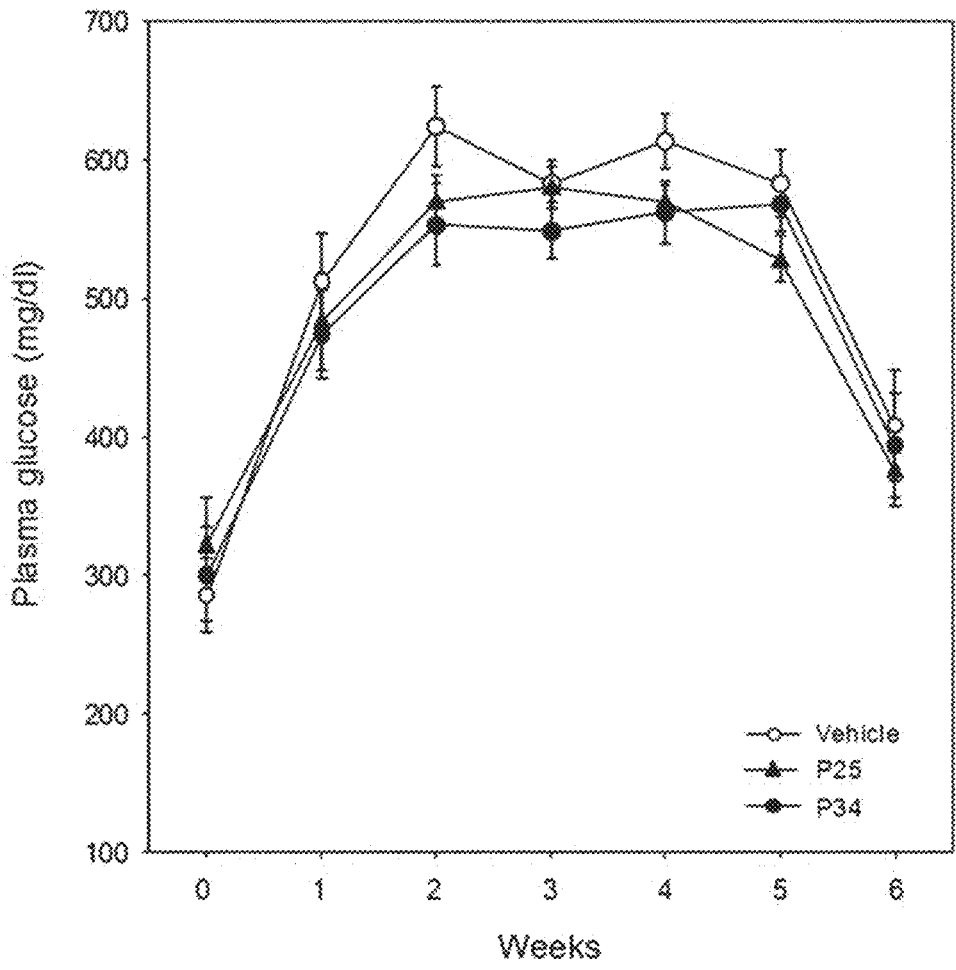
FIG. 3 is a graph confirming that a blood sugar level is reduced in P25- and P34-administered db/db mice in comparison with an excipient-administered group.

As a result, as shown in FIG. 3, it can be confirmed that an approximate 6 to 9% decrease in blood glucose was shown at week 1 to 5 in the P25-administered group, and an approximate 7 to 11% decrease in blood glucose was shown at week 1 to 5 in the P34-administered group.

Example 2. Confirmation of Effect of LGI3-Derived Peptide on Pancreas, Indices in Blood, and Insulin Resistance in Diabetic Animal Model

Example 2-1. Confirmation of Pancreatic Weight and Histopathological Change by Administration of LGI3-Derived Peptide Autopsy was performed to confirm the effect of the P25 or P34 administered into the db/db mice in Example 1-1 on the pancreas. The animals were fasted (water provided) for about 16 hours before autopsy. At the time of autopsy, the animals were anesthetized by inhalation with isoflurane, followed by laparotomy and blood collection from the posterior vena cava. After the blood collection, the abdominal aorta and posterior vena cava of the animal were cut, and the pancreas was removed from the animal, which had been exsanguinated, followed by weighing and fixation in a 10% neutral buffered formalin solution. The fixed pancreas was stained by H&E staining, and a pancreatic islet number, islets of pancreatic tissue/cm$^2$ and the diameter of the pancreatic islet (μm), and the proportion of zymogen granules per unit area of the pancreatic exocrine (zymogen granules %/mm$^2$ of exocrine) were analyzed, and image analysis was performed using an image analysis program (iSolution EL ver 9.1, IMT i-solution Inc., Quebec, Canada).

Figure 4A:
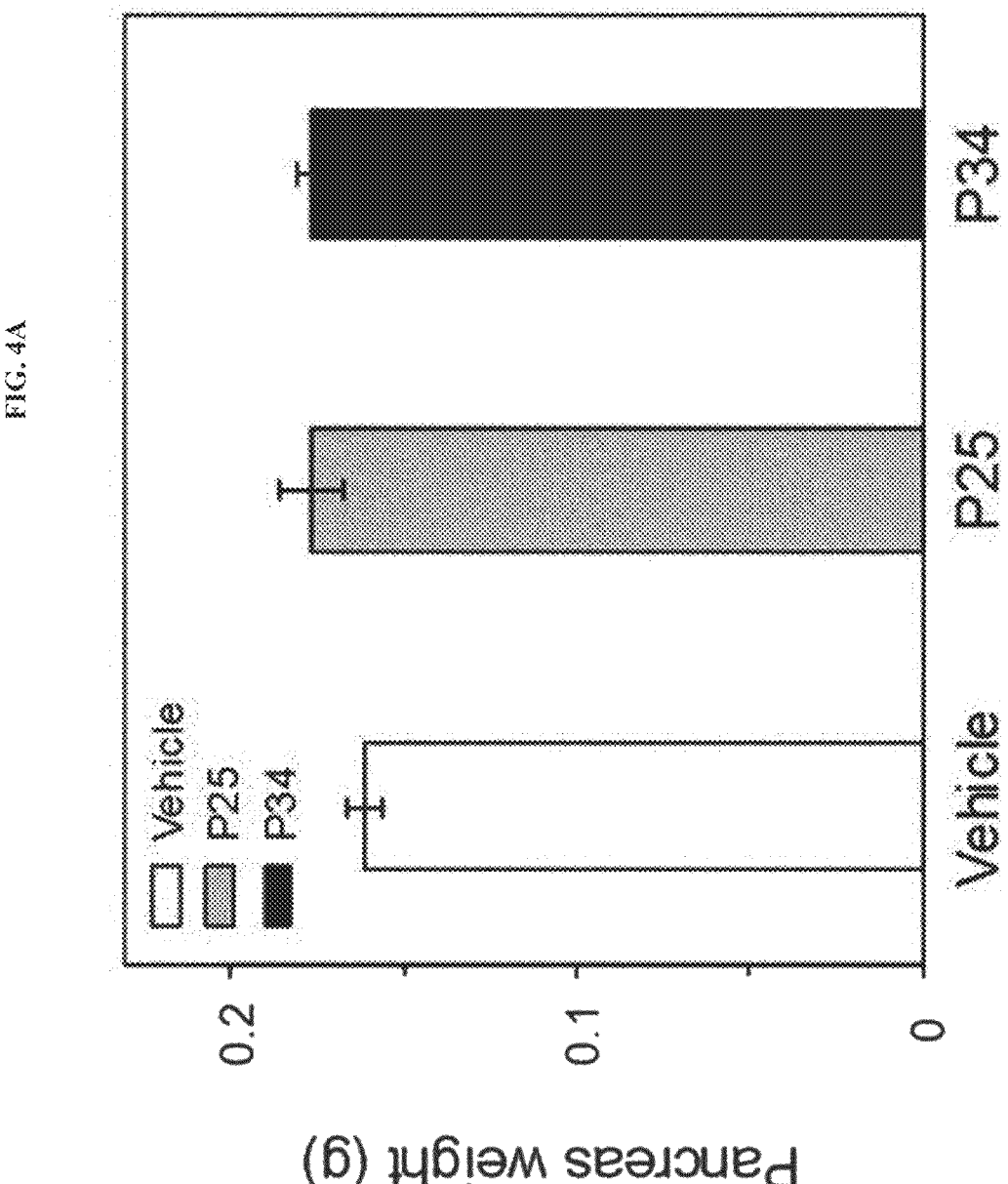
FIG. 4A is a graph confirming that a pancreatic weight is increased in P25- and P34-administered db/db mice in comparison with an excipient-administered group.

As a result, as shown in FIG. 4A, an approximate 9% increase in pancreatic weight was confirmed in the P25- and P34-administered groups, compared to the excipient-administered group.

Figure 4B:
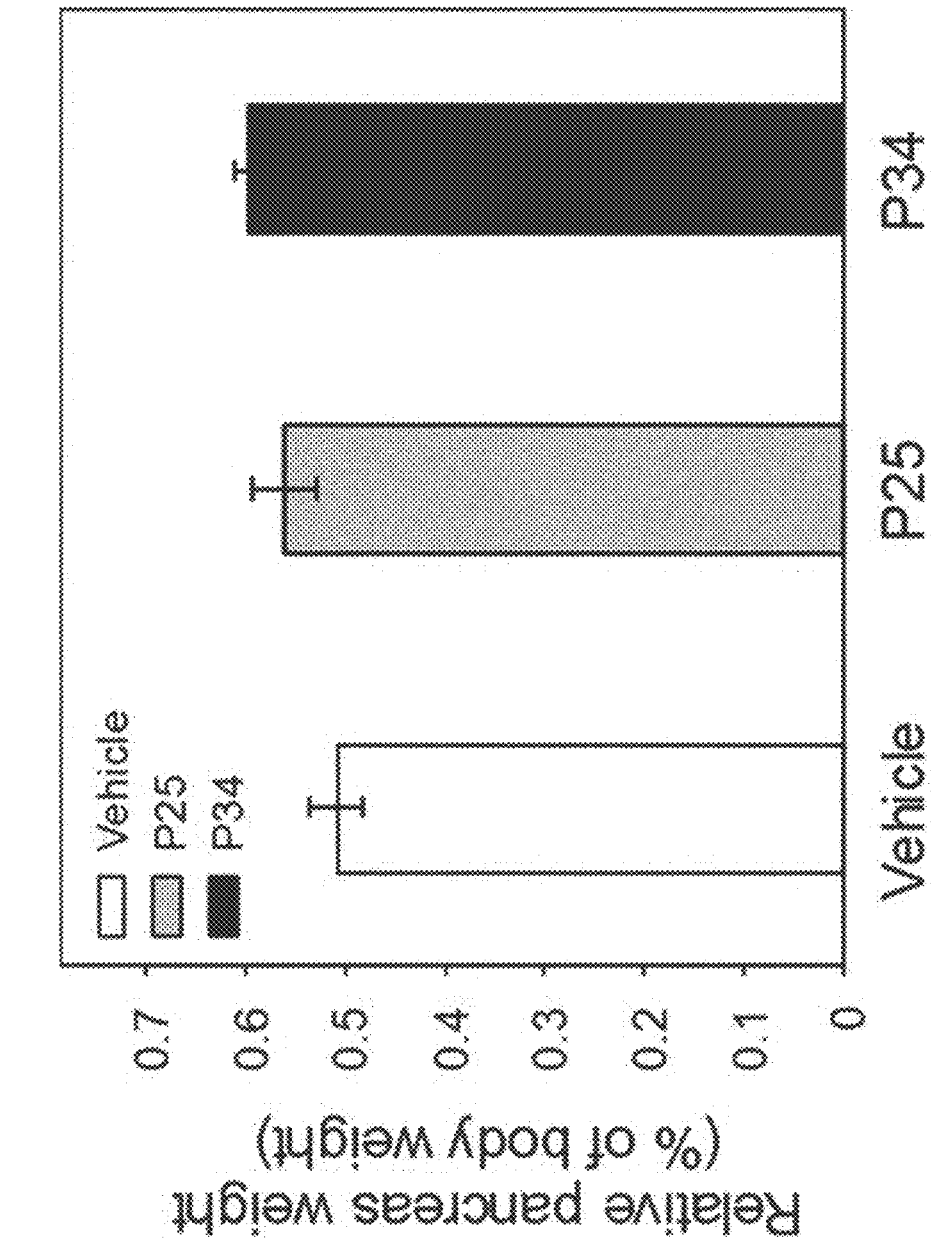
FIG. 4B is a graph confirming that % weight based on a pancreatic weight is increased in P25- and P34-administered db/db mice in comparison with an excipient-administered group.

As shown in FIG. 4B, approximate 10% and 17% increases in % pancreatic weight relative to body weight were confirmed in the P25- and P34-administered groups, respectively.

As a result of histopathological examination, as shown in FIGS. 5A and 5B, compared to the excipient-administered group, changes in pancreatic islet numbers (islets/cm$^2$) and diameters (μm) in the P25-administered group and P34-administered group were not observed, and significant increases in the proportion of zymogen granules per unit area of the pancreatic exocrine (zymogen granules %/mm$^2$ of exocrine) were observed in the P25- and P34-administered groups.

These results show that P25 and P34 have therapeutic and alleviating effects on pancreatic exocrine insufficiency generated in diabetes.

Example 2-2. Confirmation of Effect on Indices in Blood by Administration of LGI3-Derived Peptide To confirm the effect of the P25 or P34 administered into the db/db mice in Example 1-1 on indices in blood, glycated hemoglobin (HbA1c) and total cholesterol (TCHOL), triglyceride (TG), low density lipoprotein (LDL), high density lipoprotein (HDL), aspartate aminotransferase (AST), and alanine aminotransferase (ALT) were measured, and the TG/HDL ratio and the LDL/HDL ratio were calculated.

Figure 6A:
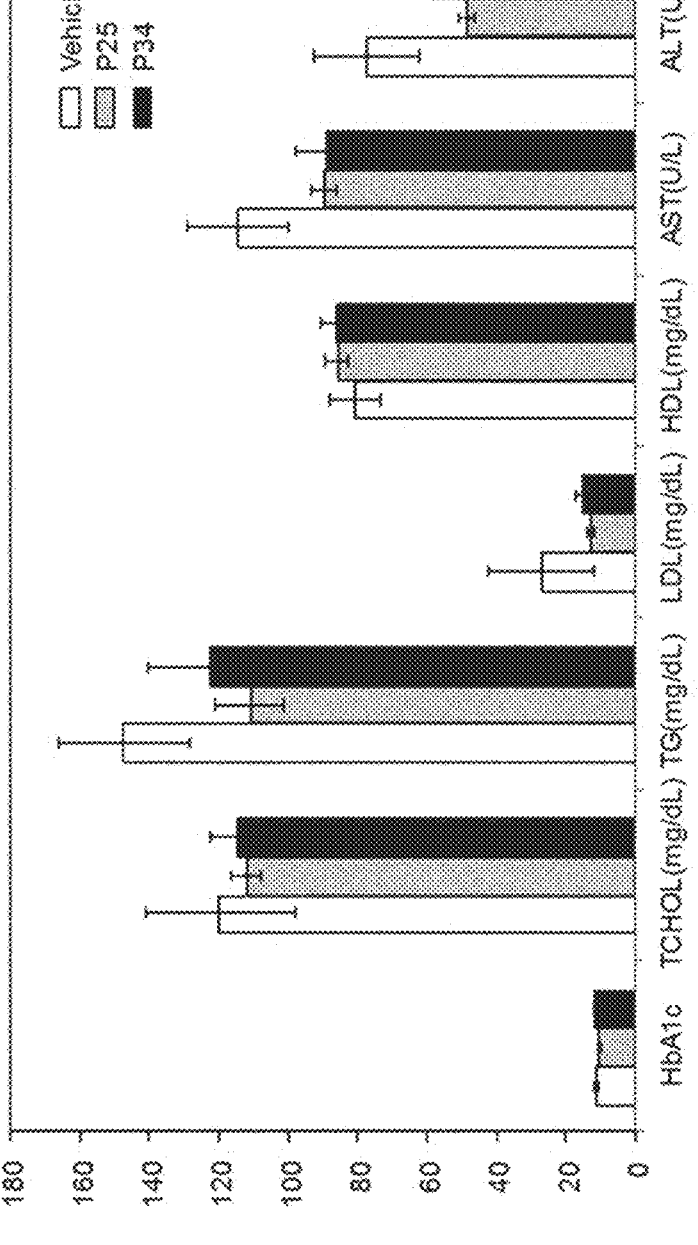
FIG. 6A is a graph confirming changes in glycated hemoglobin (HbA1c) and total cholesterol (TCHOL), triglyceride (TG), low density lipoprotein (LDL), high density lipoprotein (HDL), aspartate aminotransferase (AST), and alanine aminotransferase (ALT) in P25- and P34-administered db/db mice in comparison with an excipient-administered group.

As a result, as shown in FIG. 6A, it can be confirmed that the blood TG, LDL, AST and ALT were reduced in both of the P25-administered group and the P34-administered group, compared to the excipient-administered group, showing that a blood lipid improving effect and a liver function protecting effect can be achieved by P25 or P34 administration.

Figure 6B:
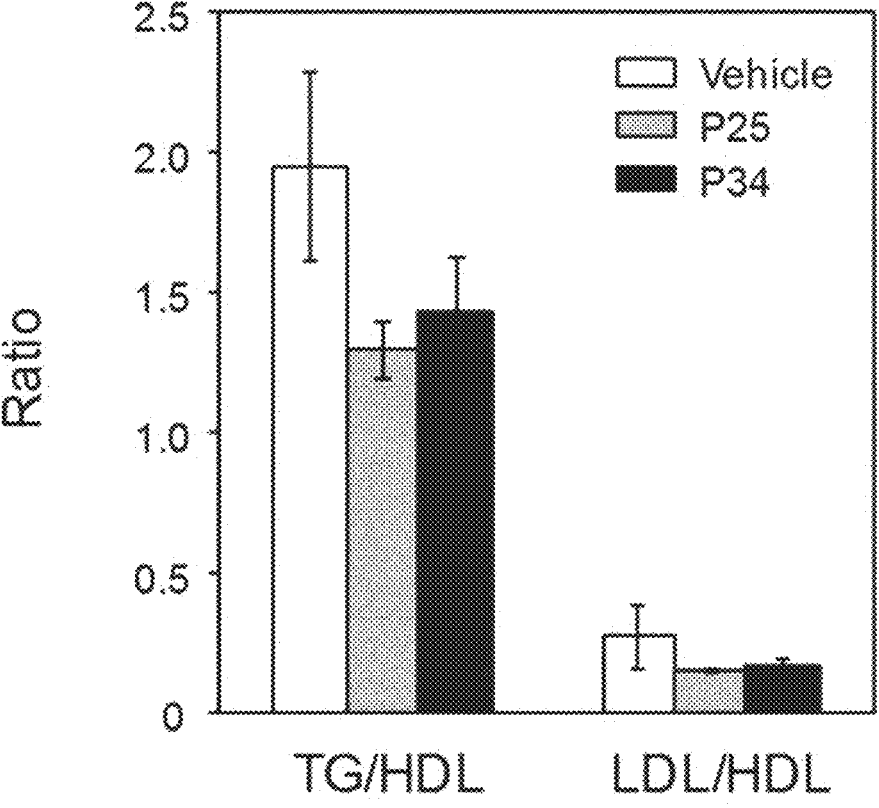
FIG. 6B is a graph confirming that a triglyceride/high density lipoprotein ratio (TG/HDL) and a low density lipoprotein/high density lipoprotein ratio (LDL/HDL) are reduced and improved in P25- and P34-administered db/db mice in comparison with an excipient-administered group.

In addition, as shown in FIG. 6B, it can be confirmed that the TG/HDL ratio and the LDL/HDL ratio were reduced in both of the P25-administered group and the P34-administered group, showing that the blood lipid improving effect can be achieved by P25 or P34 administration.

Example 2-3. Confirmation of Effect on Insulin Resistance Index by Administration of LGI3-Derived Peptide To confirm the effect of the P25 or P34 administered into the db/db mice in Example 1-1 on the insulin resistance index, serum insulin was quantitatively analyzed using an ELISA kit (Shibayagi, AKRIN-011T). An insulin resistance index (HOMA-IR=[fasting insulin (μIU/mL)×fasting blood glucose (mmol/L)]/22.5) was calculated from the insulin concentration and blood sugar level, which had been quantitatively analyzed.

As a result, as shown in FIG. 7A, it was confirmed that the blood insulin levels were reduced and improved in both of the P25-administered group and the P34-administered group, compared to the excipient-administered group, and as shown in FIG. 7B, the insulin resistance index (HOMA-IR) was reduced and improved in the P25-administered group and the P34-administered group, compared to the control.

Collectively, the inventors confirmed that the LGI3-derived peptides, P25 (QNGFYSHQALHAWHR, SEQ ID NO: 1) and P34 (DEGRQKFVRFQELAV, SEQ ID NO: 2), have a diabetes treatment and alleviation effect in the db/db mice. Particularly, as the P34 peptide showed a weight loss effect, and the P25 and P34 peptides showed not only blood sugar and insulin resistance index improvement effects, but also showed effects of treating and improving diabetes-associated symptoms, such as pancreatic damage and blood lipids (triglycerides, LDL and HDL) and abnormal liver functions (AST and ALT), it can be seen that the P24 and P34, which are LGI3-derived peptides controlling LGI3 activity, can be used in drugs and health functional foods for preventing, treating or alleviating diabetes and a diabetes-associated metabolic disorder and lead materials for developing the same.

It should be understood by those of ordinary skill in the art that the above description of the present invention is exemplary, and the exemplary embodiments disclosed herein can be easily modified into other specific forms without departing from the technical spirit or essential features of the present invention. Therefore, the exemplary embodiments described above should be interpreted as illustrative and not limited in any aspect.

INDUSTRIAL APPLICABILITY

A composition comprising an LGI3-derived peptide as an active ingredient according to the present invention may prevent, treat or alleviate various types of metabolic disorders caused by diabetes by promoting reductions in body weight and blood sugar, which are main causes of diabetes and a diabetes-associated metabolic disorder, reducing pan-creatic damage, improving a blood lipid composition and a liver function index, reducing blood insulin and improving insulin resistance.

In addition, the composition of the present invention induces improvements in blood sugar and insulin resistance without an anorectic action, and has an advantage of no or few side effects shown by conventional therapeutic agents for diabetes. Accordingly, the LGI3-derived peptide of the present invention and materials that can be developed by using it as a lead material are expected to be used in various aspects such as compositions for drugs, quasi-drugs, food additives, and fragrances and cosmetics for preventing and treating diabetes and related metabolic disorders thereof, and thus has industrial applicability.

---

The invention claimed is:

1. A method of treating pancreatic exocrine insufficiency generated in diabetes in a subject comprising:

administering a pharmaceutically effective amount of a composition comprising a leucine-rich repeat LGI family member 3 (LGI3)-derived peptide comprising an amino acid sequence represented by SEQ ID NO: 1 or SEQ ID NO: 2 as an active ingredient into the subject, and wherein the LGI3-derived peptide increases zymogen granules of the pancreas and pancreatic weight, and reduces a blood sugar level.

2. A method of treating a diabetes-associated metabolic disorder in a subject by administering a pharmaceutical composition comprising an effective amount a leucine-rich repeat LGI family member 3 (LGI3)-derived peptide comprising an amino acid sequence represented by SEQ ID NO: 1 or SEQ ID NO: 2 as an active ingredient into the subject wherein the diabetes-associated metabolic disorder is one or more selected from the group consisting of hyperglycemia, liver damage associated with an elevated aspartate aminotransferase (AST) level, and pancreatic damage.

* * * * *